United States Patent
Leonard et al.

(10) Patent No.: US 10,121,188 B2
(45) Date of Patent: Nov. 6, 2018

(54) METHOD FOR ORDERING A SPECTACLE LENS AND ASSOCIATED SYSTEM

(71) Applicant: Essilor International, Charenton le Pont (FR)

(72) Inventors: Eric Leonard, Charenton le Pont (FR); Ahmed Haddadi, Charenton le Pont (FR)

(73) Assignee: Essilor International, Charenton le Pont (FR)

( * ) Notice: Subject to any disclaimer, the term of this patent is extended or adjusted under 35 U.S.C. 154(b) by 623 days.

(21) Appl. No.: 14/383,869

(22) PCT Filed: Mar. 8, 2013

(86) PCT No.: PCT/EP2013/054688
§ 371 (c)(1),
(2) Date: Sep. 8, 2014

(87) PCT Pub. No.: WO2013/132049
PCT Pub. Date: Sep. 12, 2013

(65) Prior Publication Data
US 2015/0019389 A1  Jan. 15, 2015

(30) Foreign Application Priority Data
Mar. 8, 2012 (EP) .................................... 12290082

(51) Int. Cl.
*G06Q 30/00* (2012.01)
*G06Q 30/06* (2012.01)
(Continued)

(52) U.S. Cl.
CPC ....... *G06Q 30/0643* (2013.01); *A61B 3/0083* (2013.01); *G06F 19/00* (2013.01);
(Continued)

(58) Field of Classification Search
CPC ........... G06Q 30/06; G06Q 30/0601–30/0643; G06Q 30/08; G02C 13/003; G02C 13/005;
(Continued)

(56) References Cited

U.S. PATENT DOCUMENTS

| 5,617,155 A | 4/1997 | Ducarouge |
| 6,382,789 B1 | 5/2002 | Baudart |

(Continued)

FOREIGN PATENT DOCUMENTS

| EP | 0680722 | 11/1995 |
| EP | 0851265 | 7/1998 |

(Continued)

OTHER PUBLICATIONS

Try on New Glasses in Warby Parker's Virtual Booth. Jason Fitzpatrick. May 7, 2010. (Year: 2010).*

*Primary Examiner* — William J Allen
(74) *Attorney, Agent, or Firm* — Oblon, McClelland, Maier & Neustadt, L.L.P.

(57) ABSTRACT

A method and an associated system for ordering a spectacle lens by a wearer (1), said method involving steps of: selecting (S1) a spectacle frame by the wearer (1); capturing (S2) a picture showing partially a face of said wearer (1) wearing the selected spectacle frame, at a picture capturing side (10) so as a position of said spectacle frame with respect to the wearer face is extractable from said picture; obtaining (S3.1) a three dimensional shape of the selected frame at said picture processing side (20); processing (S3) said picture for obtaining the position of said spectacle frame with respect to the wearer face at said picture processing side (20); and ordering (S6) to a lens manufacturing side (40) spectacle lens complying with said frame shape, said extracted frame position, and wearer data, wherein said (Continued)

wearer data comprises at least a prescription for the wearer (1).

6 Claims, 5 Drawing Sheets

(51) Int. Cl.
*A61B 3/00* (2006.01)
*G06F 19/00* (2018.01)
*G02C 3/00* (2006.01)
*A61B 3/11* (2006.01)

(52) U.S. Cl.
CPC ..... *G06F 19/3456* (2013.01); *G06Q 30/0621* (2013.01); *G06Q 30/0623* (2013.01); *A61B 3/11* (2013.01); *G02C 3/003* (2013.01)

(58) Field of Classification Search
CPC ..... A61B 3/00; A61B 3/0008; A61B 3/00083; A61B 3/10; A61B 3/1005; A61B 3/11; A61B 3/117; A61B 3/14; A61B 3/145
See application file for complete search history.

(56) References Cited

U.S. PATENT DOCUMENTS

| | | | |
|---|---|---|---|
| 2003/0090625 A1 | 5/2003 | Izumitani et al. | |
| 2003/0200155 A1* | 10/2003 | Ouchi | G06Q 10/0833 705/26.62 |
| 2004/0004633 A1 | 1/2004 | Perry | |
| 2004/0015412 A1* | 1/2004 | Shinbo | G02C 7/041 705/26.41 |
| 2009/0051871 A1* | 2/2009 | Warden | G02C 13/005 351/204 |
| 2009/0263115 A1* | 10/2009 | Suzuki | A61B 3/14 396/18 |
| 2010/0283844 A1* | 11/2010 | Sayag | G02C 13/003 348/78 |
| 2011/0258071 A1* | 10/2011 | Wada | G02C 7/066 705/26.7 |

FOREIGN PATENT DOCUMENTS

| | | |
|---|---|---|
| EP | 0990939 | 4/2000 |
| EP | 1 336 924 | 8/2003 |
| EP | 1 967 894 | 9/2008 |

\* cited by examiner

METHOD FOR ORDERING A SPECTACLE LENS AND ASSOCIATED SYSTEM

RELATED APPLICATIONS

This application is a U.S. National Phase Application under 35 USC 371 of International Application PCT/EP2013/054688 filed Mar. 8, 2013.

This application claims the priority of French application No. 12290082.2 filed Mar. 8, 2012, the entire content of which is hereby incorporated by reference.

FIELD OF THE INVENTION

The present invention relates to a method and an associated system for ordering a spectacle lens. More particularly, the invention concerns a method for ordering by a wearer a spectacle lens adapted to a spectacle frame selected by said wearer when a prescription for said spectacle lens is known.

BACKGROUND OF THE INVENTION

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

When a person requires a pair of spectacles, he usually visits successively an optometrist for an eye exam and an optician who is on hand to assist him in selecting and fitting the new spectacles. In particular, the optician must realize certain measurements on position of said spectacle frame with respect to the eyes of the person and gathers the results of these measurements with other data needed to produce the lens adapted to the need and the wishes of the person. One of the tasks of the optician is to check the consistency of the selection of frame, lens options and prescription.

Figure 1:
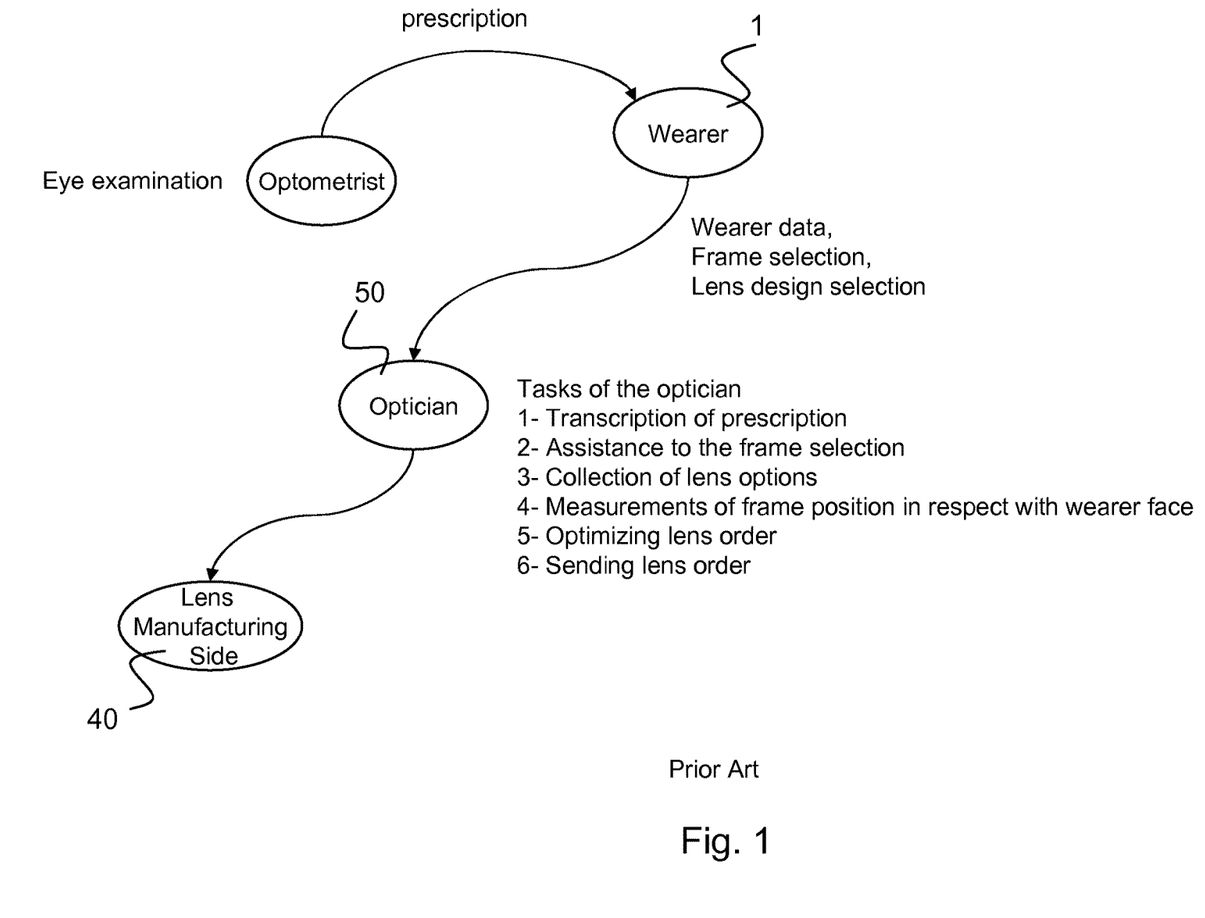
FIG. 1, already described above, shows the data flows in a process of lens ordering according to the prior art.

More particularly, FIG. 1 illustrates the data flow of the process of ordering spectacle lens according to the prior art.

First, the person (depicted as "wearer" below) goes to an eye exam at an optometrist and gets from the optometrist a lens prescription generally on a hand-written form. Then, the wearer visits the optician for selecting spectacle frame and spectacle lenses for equipping the selected frame. For that, the wearer brings the lens prescription to the optician. Conventionally, the optician directly measures the various parameters on the spectacle wearer, using a measuring instrument. Another disadvantage is that the measurements are not taken in the natural position for the spectacle wearer, but rather at a position for which the spectacle wearer is somewhat constrained, with his head being kept at a fixed position, various measuring devices being present in the visual field, etc. The optician compiles the prescription, the frame selected by the wearer and the lens options selected by the wearer (lens weight and thickness, scratch coating and impact resistance, tint color, anti-reflection coating, and multi-focal lenses, etc. . . . ). Generally, the optician provides advices to the wearer for optimizing the frame selection with respect to the lens prescription and the lens options on the basis of the various wearer selections.

This whole process can be long: it involves a transcription and a check of the lens prescription by the optician and a review of many different frames made physically available to the wearer by the optician. Then, the optician has further to collect the lens options selected by the wearer.

At least, once a frame is selected, the optician also generates a set of data required for designing a spectacle lens. These data have various types and comprise at least: 1/ wearer data including prescription data and wearer lens options, 2/ frame data describing the geometry of the frame selected by the wearer and finally 3/ position information related to the frame position with respect to the face of the wearer at wearing time. From a careful analysis of this set of data (for example consistency between frame curving contour and prescription) and by checking in lens manufacturer data books, the optician can advise the wearer on the possible trade-offs and finally orders spectacle lenses to a lens manufacturing side. The position information includes at least the distance between the pupils and the segment heights. Such measurements are critical for the proper manufacture of the eyeglasses for the selected frames. If such measurements are not properly taken, the resulting eyeglasses become useless to the customer, and time and money are wasted. Such measurements are usually taken manually with a ruler or with the aid of various measurement devices. All such methods require skill and great care to achieve acceptable accuracy. In practice, such accuracy is not always attained.

From FIG. 1, it appears that in the usual lens ordering process, a majority of tasks is concentrated at the optician side.

This tasks dispatch and the duration of these individual successive tasks do not benefit the wearer: quite often the wearer may have to wait before being helped by an optician. As he must physically try-on each of the frames selected for consideration; he must preview each tried-on frame in a mirror without wearing his right prescription lenses, which can be difficult for some and inconvenient for most. Moreover, the optician has also to perform the manual measurements mentioned above (including an acquisition of the 3D shape of the selected frame for lens edging purpose).

On another level, one observes that customers generally want to have a high degree of autonomy when they visit a store to make a purchase: They like to manipulate items, try them, wear them. Thus the wearer wishes to try pairs of glasses on his own, at his own pace. The wearers may also prefer to make their purchase at a time that is not constrained by open hours of an optician's shop, for example by selecting glasses and purchasing it at night rather than during the day. This empowerment of the client is a reality for tens of years. This is a general trend of trade leading to development of self-service stores and more services online ordering for many types of trade and services. Another advantage of the invention is to propose an organization of tasks necessary for ordering of glass and/or glasses that makes possible the satisfaction of customer requirements on autonomy.

The current organization of lens ordering process is neither convenient for the opticians because opticians have to perform a high number of non added-value and tedious jobs before ordering lens such as for example 1/ transcription of the hand-written prescription, 2/ assistance to the frame choice by customers, sometimes indecisive from a large number of frame styles and manufacturers; or 3/ once a particular frame is selected, the optician must obtain certain manual measurements in regard with the frame shape or the position of frame with respect to frame.

The European patent EP0851265B1 describes a method for reducing the duration of the step of obtaining precise frame shape information for edging purpose without measuring the shape of a spectacle frame in a spectacle store.

The European patent EP0680722B1 proposes a system to automatically obtain the eye/frame measurements by way of pupil and frame detection. In this method the image is scaled due to the presence of a scale of a known size inside the image enabling the magnification factor of the image (knowing the focal length, etc.) to be determined.

But, none of these documents does propose a global task dispatch for shortening the whole process of lens ordering which reduces significantly the workload of the optician.

SUMMARY OF THE INVENTION

One object of the present invention is to relieve the optician of some of the sequential tasks mentioned above by proposing new data collection architectures configured for gathering all data required for designing a lens at a manufacturing unit. A first solution includes carrying out part of tasks previously realized by opticians bypassing the opticians. Both opticians and the wearers could benefit of this new data flow organization. A second solution, which is not incompatible with first solution, includes simplifying and reducing the burden of these individual tasks still in the goal of reducing the global workload of the optician and increase his availability for welcoming new wearers.

Another object of the invention is to perform the measurements mentioned above automatically with a high accuracy and high liability with no increase of the workload of the opticians.

These and other objects are attained in accordance with one aspect of the present invention directed to a method, implemented by computer means, for ordering a spectacle lens by a wearer 1, said method involving steps of:

Selecting S1 a spectacle frame by the wearer 1, at a picture capturing side (10);
Capturing S2 at least one picture showing at least partially a face of said wearer wearing the selected spectacle frame, at said picture capturing side 10 so as a position of said spectacle frame with respect to the wearer face is extractable from said at least one picture;
Obtaining S3.1 a three dimensional shape of the selected frame at said picture processing side 20,
Processing S3 said at least one picture for obtaining the position of said spectacle frame with respect to the wearer face at said picture processing side 20, and
Ordering S6 to a lens manufacturing side 40 spectacle lens complying with said frame shape, said extracted frame position, and wearer data at an order side 50, wherein said wearer data comprise at least a prescription for the wearer 1.

The present invention concerns according to a second aspect a system for supplying a spectacle lens, said system comprising:

means 5 for selecting a spectacle frame by the wearer 1;
means 10 for capturing at least one picture showing at least partially the face of said wearer 1 wearing the selected spectacle frame, so as a position of said spectacle frame with respect to the wearer face is extractable from said at least one captured picture;
means 20, 25 for obtaining a three dimensional shape of the selected frame;
means 20 for processing said at least one picture for obtaining an extracted spectacle frame position;
means 50 for ordering to a lens manufacturer 40 said spectacle lens complying with fitting parameters and said wearer data, wherein said fitting parameters comprising at least said extracted frame position and said obtained frame shape.

BRIEF DESCRIPTION OF THE DRAWINGS

The invention will be better understood and illustrated by means of the following embodiments and execution examples, in no way limitative, with reference to the appended figures on which.

DETAILED DESCRIPTION OF PREFERRED EMBODIMENTS

It is to be understood that the figures and descriptions of the present invention have been simplified to illustrate elements that are relevant for a clear understanding of the present invention, while eliminating, for purposes of clarity, many other elements found in typical spectacle lens ordering methods and systems. However, because such elements are well known in the art, a detailed discussion of such elements is not provided herein. The disclosure herein is directed to all such variations and modifications known to those skilled in the art.

There are two main scenarios for a wearer having a lens prescription who wants to order spectacle lens according an embodiment of the invention:

The wearer lives in a big town or close to an optician shop: then it is convenient for him to go to this optician shop. The optician validates the selection of the wearer and checks their consistency. The optician relies on new tools for performing his job lightening his workload.

The wearer lives far from any optician shop or near optician shop open at hours not compatible whit his own free time. For selecting and ordering lens or spectacle, he can enter a frame selection place (detailed below) where no optician is present but which is open at large hours. The wearer can first select a spectacle frame and carries out the supplementary steps of the lens ordering process without any assistance of a person present in this frame selection place. The wearer selections are validated remotely, e.g. via internet or other communication means, by experts or by expert systems located for example in a different continent than the wearer.

Figure 2:
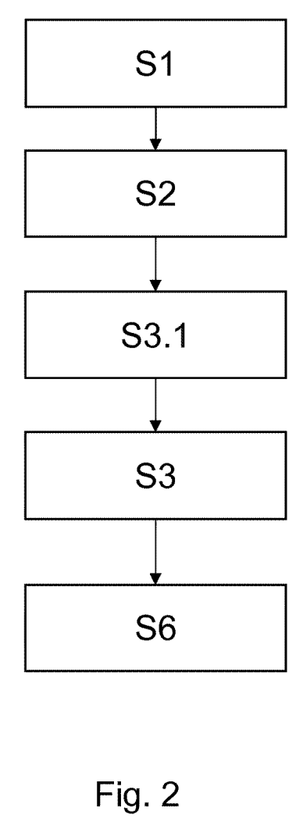
FIG. 2 is a flow chart illustrating an embodiment of the method.

FIG. 2 is a flow chart of an embodiment of the method which can be carried out in the two above mentioned scenarios.

S1 is a step of selecting a spectacle frame by a wearer 1. The place where the wearer selects his frame is either an optician shop or another place equipped with a large choice of trial spectacles as explained below. Preferably this place comprises means for communicating the frame selection.

S2 is a step of capturing at least one picture showing at least partially a face of the wearer wearing the selected spectacle frame. The picture capturing side is, in general, the frame selection place. This step is an extra step which was not carried out in prior art lens ordering processes. It is carried out at a picture capturing side 10 so as at least the position of said spectacle frame with respect to the wearer face is extractable from said at least one picture. The wearer captures on his own the pictures by standing in front of a camera. Advantageously a graphical user interface assists the wearer for capturing pictures. This point will be further detailed later.

S3.1 is a step of obtaining a three dimensional shape of the selected frame. This step can be carried out by the optician or by the wearer still at the frame selection place by known means and methods. It can also be performed at remote image processing side 20 if the picture capturing side and the picture processing sides are connected by communication means for transferring the captured pictures. Then, as discussed later in more detailed, the frame shape can be extracted automatically from a captured picture if a tag is placed beforehand on the trial spectacle. Then, an extraction of the three dimensional shape is computed by numerical image processing by automatically reading data comprised in the tag. The frame shape extraction is indirect or direct that is by sending a request to a frame database 25 or not. The advantage of the acquisition of frame shape by an extraction from the captured image is that it doesn't require any manual action form the optician.

For facilitating the frame database maintenance and for reducing the cost of maintenance, the frame database is usually a centralized instance.

In case where the frame shape is extracted remotely, it is important that preliminary checks are performed short time after the capture time in order to inform the wearer whether the captured picture is compliant or not with the frame shape extraction. This enables to capture extra picture and potentially save time for the wearer. These preliminary checks are not shown on FIG. 2, but are figured on FIG. 3 by a dashed arrow from the picture processing side 30 to the picture capturing side 20. This dashed arrow was not shown on FIG. 4 for improving the intelligibility of the FIG. 4.

S3 is a step of processing the captured picture for obtaining the position of said spectacle frame with respect to the eyes of the wearer, that is "with respect to the wearer face". This step is carried out at a picture processing side 20. The position information is also extracted from at least a captured picture by numerical image processing. This processing relies on the frame shape determined at step 3.1 for obtaining a distance scale in the captured picture. Methods for extracting height of pupilla in the frame and interpupilla distance are known and shown for example in the European patent EP0680722B1. There are alternative methods enabling acquisition of more refined fitting parameters such as the pantoscopic angle of the frame and the glass-eye distance which can be used for designing lens as described patent application EP0990939B1.

It is also important that other preliminary checks are performed short time after the capture time in order to inform the wearer whether the captured picture is compliant or not with the position information extraction. This enables to capture extra picture and potentially save time for the wearer. Advantageously, preliminary checks are performed at once when the frame shape and the position information is extracted from captured picture. These other preliminary checks are not shown on FIG. 2, but are figured on FIG. 3 by a dashed arrow from the picture processing side 30 to the picture capturing side 20. This dashed arrow was not shown on FIG. 4 for improving the intelligibility of the FIG. 4.

S6 is a step of ordering a spectacle lens to a lens manufacturing side, 40.

Figure 3:
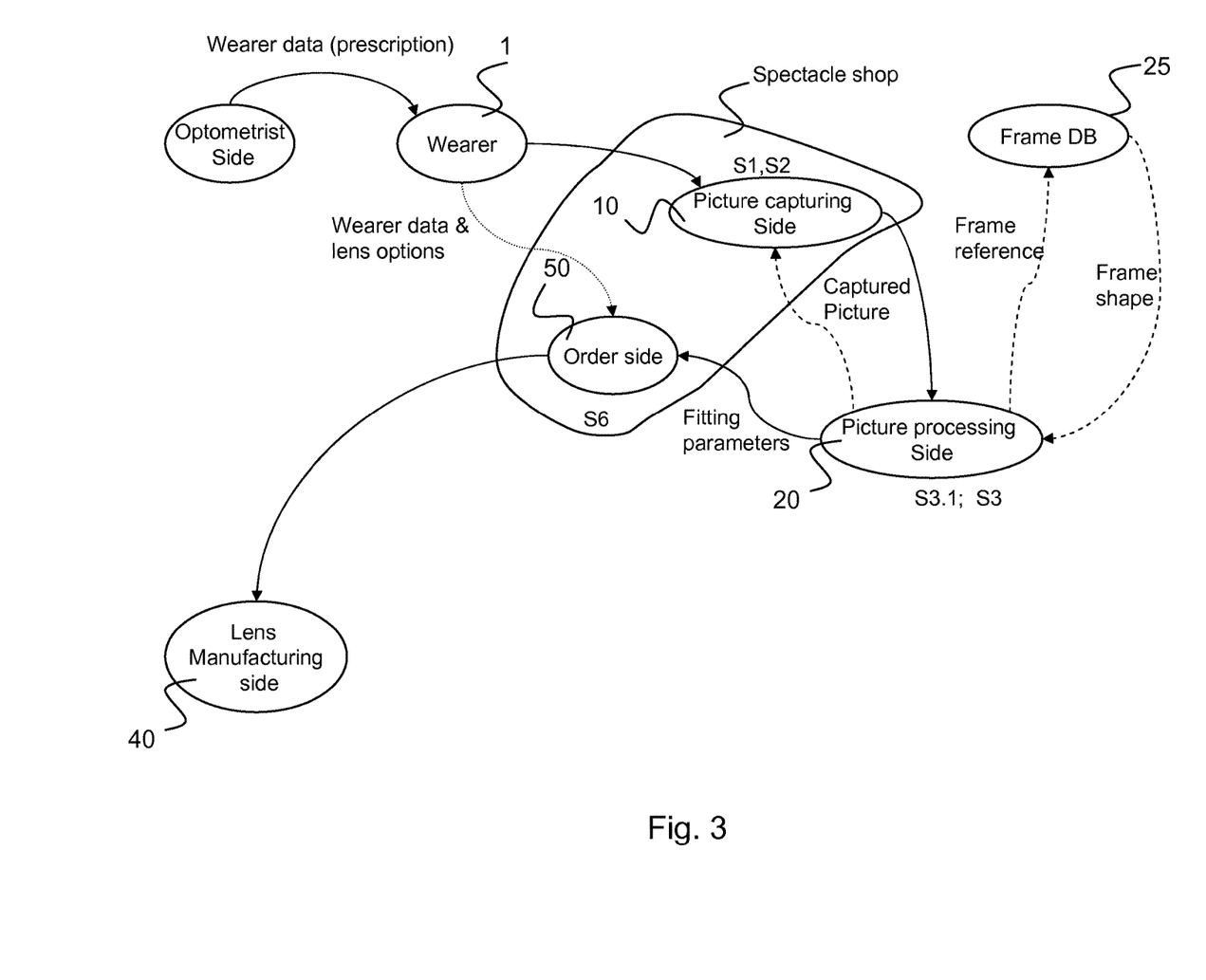
FIG. 3 shows the data flows in a process of lens ordering according to the invention in a first scenario.

In the first scenario illustrated in FIG. 3, the picture capturing side 10, and the order side are concentrated in the optician spectacle shop: step S6 is carried out there. It consists in:
Collecting and gathering data related to the selections of the wearer (wearer data, lens options data, frame shape, fitting parameters);
Checking consistency of collected data;
Selecting a lens design complying with collected data and
Ordering to a lens manufacturing side a lens according to the selected lens design.

Preferably the ordering step further comprises an ordering of selected frame, and both the ordered lens and the ordered frame are sent independently to the order side where the lens is mounted into the frame. Advantageously, the mounted frame is sent the ordering side.

Figure 4:
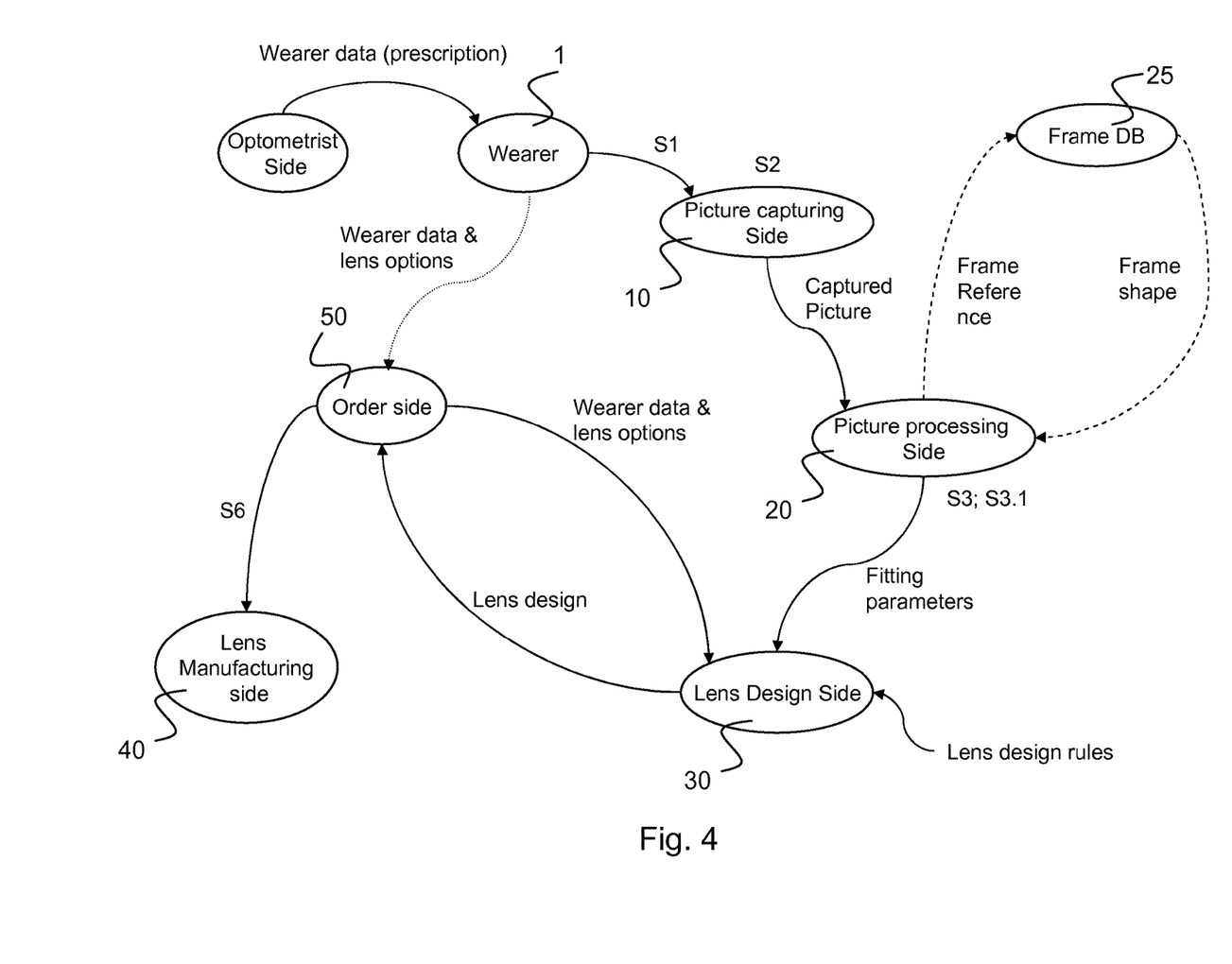
FIG. 4 shows the data flows in a process of lens ordering according to the invention in a second scenario.

In the second scenario illustrated in FIG. 4, the picture capturing side 10, the picture processing side 20, the frame database 25, the lens design side 30, the lens order side, 50, and the lens manufacturing side 40 are located in various locations even on different continent. Next, steps carried out consist in:
Collecting and gathering data related to the selections of the wearer (wearer data, lens options data, frame shape, fitting parameters) at a lens design site 30;
Selecting a lens design by performing a trade-off between collected data and from design rules, at this lens design site 30;
Ordering to a lens manufacturing side a lens according to the selected lens design.

Because on this second scenario, the workload of the optician is reduced to zero, it enables the wearer to order a spectacle frame without the presence of any optician at his sides.

FIG. 3 and FIG. 4 are two diagrams illustrating an outline of the method of ordering spectacle lens, which is a first embodiment of the present invention in the first scenario and the second scenario. Hereinafter, this method and a system for carrying out this method will be described in detail by referring to FIGS. 3 & 4 which differ mainly by the place from where the lens ordered to the lens manufacturing side.

As is illustrated in the FIG. 4, this method of ordering spectacle lens, namely, the first embodiment of the present invention comprises: (S1) a step of selecting frame by the wearer; (S3.1) a step of acquiring an actual frame shape; (S3) a step of measuring the position of said spectacle frame with respect to the wearer face; (S6) lens processing step; and (S7) a lens manufacturing step.

Hereunder, all these steps will be described in more detail and more particularly the place where it is carried out is discussed.

A step S00 (not shown on FIG. 2) of inputting wearer data including a prescription realized by an optometrist for his both eyes and at least personal data of the wearer is carried out before step S1.

(S00) Input the Wearer Data

As recalled above, a person, later identified as a "wearer", who wants a new spectacle, has first to get a lens prescription from an optometrist. If the wearer wants to change his spectacle due to a frame or a lens break he can get the information on lens prescription from his optician who usually had stored it. If the lens is safe, every optician usually has the means for retrieving the lens prescription from a lens study. The prescription issued by the optometrist is usually handwritten on a paper form and the first task of the optician when a wearer enters consists in transcripting the writing of the optometrist on a numerical support, for example by inputting information through keyboard operation. Additionally, the optician gets personal wearer data as its identity, its address, and its insurance reference number directly from the wearer. Then, the optician fills a file gathering both personal wearer data and prescription information. Hereafter, both prescription information and personal wear data will be gathered and described as "wearer data".

Advantageously the optometrist has previously added on the prescription form he delivered a two-dimensional matrix barcode consisting of black and white "cells" or modules arranged in either a square or rectangular pattern. The information to be encoded can be text or raw data such as the prescription and said personal wearer data. Usual data size is from a few bytes up to 1000 bytes. The length of the encoded data depends on the symbol dimension used. Error correction codes are added to increase symbol strength: even if the two-dimensional matrix barcode are damaged or partially read, their content can still be read. This barcode is either of type QR Code® or datamatrix, Shot code, Colorzip or Maxi code, . . . . In this case the optician gets the wearer data in an easier way: directly from the smart code via a device for reading such a 2D smart code.

Advantageously in this last case, the wearer data entry can be realized either by an optician at its spectacle shop when it is equipped with previously mentioned 2D code reader either by the wearer himself who scans or gets a picture of the paper form and sends it to a software setup on communication means (personal computer, smart phone or tablet).

Another step S01 (not shown in FIG. 2) of selecting lens options by the wearer follows step S00 and precedes also step S1.

(S01) The Wearer Selects Lens Options

Additionally, the wearer also expresses choices or needs related to the lens such as a lens weight and thickness, scratch coating and impact resistance, tint colour, anti-reflection coating etc. These lens options selections are entered either directly by the wearer who fills a lens options form proposed by the optician in its shop or via a graphical user-interface available on a peripheral during a completely remote lens ordering process, either by the optician himself when the wearer enters the optician shop.

(S1) the Wearer Selects a Spectacle Frame

This step is performed in a place where a large choice of trial spectacles is available. The frame selection place further comprises at least a mirror for helping the wearer to choose the frame. Advantageously it further comprises means for capturing a picture of the wearer wearing the trial spectacle and means for showing said captured picture to the wearer. This place can be either an optician shop containing very high number of trial spectacles (e.g more than one thousand), either a kiosk containing more number of trial spectacles (e.g. between fifty and two hundred). Such a kiosk is intended to be easily movable, e.g. in traffic. The kiosk is particularly suitable for mobile opticians working in regions of low population density where no spectacle shop is present permanently but where such kiosk can be setup easily. It is not the goal of the present document to describe in deep detail such a frame selection place but in the following one will come back on certain requirement it has to conform.

The purpose of a trial spectacle is to provide assistance for selecting a model of spectacle frame. A trial spectacle is usually equipped with non corrective lenses. In particular, the trial spectacle is not used to be fitted with corrective lenses and worn daily later by a wearer. Once the wearer has chosen a trial spectacle among the available trial spectacles, he replaces the trial spectacle on the shelf where he found it and further order the frame corresponding to the selected trial spectacle: one will call this frame the "selected frame". Each trial spectacle is associated to a frame reference for identifying a model of frame in a unique manner which is usually written on the temple of the frame.

In the frame selection place, the wearer is free to wear every available trial spectacles. He can watch his/her look on a mirror wearing said trial spectacle. Once he decided to select a frame, he can simply retain or copy the reference of the selected trial spectacle for ordering a frame having the associated frame reference.

If a frame can be ordered with different colours at a frame manufacturing place, but at the frame selection place, there is only a associated trial spectacle available only with a single colour, the wearer can choose independently the frame shape (e.g. reference of the selected trial spectacle) and a colour frame independently by indicating in addition a colour reference on a catalogue. In this particular case, the frame ordering form includes the reference of the frame model associated plus the reference of the chosen colour.

According an embodiment of the present invention, the frame selection is realized by an automatic frame shape acquisition. By "automatic", one means without any manual operation of the wearer of the optician. This step enables to determine the type of the frame (Metal or plastic frame, supra or rimless frame), and more precisely the frame curving contour and its detailed geometry. All this frame information is considered in the lens design and/or later in the lens edging operations. The automatic feature relies on capture of pictures of a picture showing at least partially a face of said wearer wearing the selected spectacle frame.

The picture capturing side comprises means for capturing a picture showing at least partially a face of said wearer wearing the selected spectacle frame and the tag enabling to get the frame shape.

One intends by "means for capturing at least one picture", a means for capturing a scene under specific lighting condition with a numerical electro-optical picture sensor (e.g. camera with CCD sensor type or CMOS Active Pixel Sensor (APS) type). Said sensor is sensitive to light in visible bandwidth and provides a picture having a numerical format enabling fast dematerialized transport in remote places and numerical image processing. But, the "means for capturing at least one picture" also comprises in a broader scope, any means for capturing of a scene enabling to retrieve the details of the tag placed on the frame (e.g electro-optic sensors sensitive in Infrared or ultraviolet bandwidth, or ultrasound image sensor).

In a first embodiment, the picture sensor is configured so as its global spatial resolution and sensitivity enable to get (directly or via image processing) all the details of a tag placed on the trial spectacle as discussed in next section. Global spatial resolution concerns the ability do distinguish details on the captured picture and is closely linked with spatial resolution features of the sensor, and of the optics of the camera.

In a second embodiment, the picture sensor is configured so as its global spatial resolution and sensitivity enables to get (directly or via image processing) the position of the frame with respect to the eyes of the wearer as discussed later.

Advantageously, said means 10 for capturing picture comprises means 10.1 for controlling lighting conditions of the wearer face when said means 10 for capturing operates.

More particularly, in the first embodiment said means 10.1 provides a first light enabling a picture capture of the tag when it is written with a special ink. This point will be further discussed later in more details.

More particularly, in the second embodiment said means 10.1 provides the wearer face with a first light enabling a picture capture. This first light has a function similar to a flash lightning for a picture camera; this first light is for example a white light. Said means 10.1 further provides a second light through at least one secondary punctual light source which is configured so as at least one specific reflection spot appears on the captured picture. As the position of said at least one secondary punctual light source is precisely determined with respect to the picture capture device and because the frame shape is determined, the position of the reflection parts (corneas of the wearer and on the lens on the trial spectacle) can be retrieved from the position of the spots in the captured picture.

It is advantageous that several pictures are captured for the purpose of enabling statistical image processing and improving therefore the positioning of the spots in the captured picture.

It is advantageous that the position of said at least one secondary punctual light source is modified with respect to the wearer face for different picture capture: preferably due to a move of the wearer with respect to the camera, a move of the light source still with respect to the camera, or due to both simultaneous moves.

It is also advantageous that an additional imaging system placed in the area of the means for picture capturing supplies to the means for picture processing additional information on position of the wearer at the capture time for the purpose of accelerating the extraction of frame position. For example, this additional imaging system produces and detects ultrasound waves.

Advantageously, said means 10 for capturing picture comprises means 10.2 for controlling wearer background conditions of said at least one picture when said means (10) for capturing picture operates.

It is needless to say that the picture captured at the picture capturing side 10 for the purpose of obtaining the position of the spectacle frame with respect to the wearer face can also be used for the purpose of extracting the spectacle frame shape and vice versa for some embodiment of the invention.

For other embodiments, the frame shape is extracted from a first picture capture under a first lighting condition and then the position of the frame is extracted from a second picture capture under a second lighting condition.

(S3.1) A Frame Shape is Obtained at Picture Processing Side with/without a Connection to a Frame Database.

In advantageous embodiments, this step can be performed using a known method where the geometrical shape of frames is beforehand measured and stored in a centralized frame database, located for example at a frame manufacturing side. All the opticians are connected to this centralized frame database which comprises all the (three dimensional) geometrical data of the frames required by an optician for ordering a lens and for edging and mounting said lens in this frame. The frame database is indexed, for example, with the frame reference. For each trial spectacle, a frame reference is inserted into a barcode similar to various barcodes described above for transcripting prescriptions. Then said barcode is stuck onto the frame of the trial spectacle e.g. on one of the temples of the selected trial spectacle. In its spectacle shop, the optician reads the barcode stuck on the frame of the selected trial spectacle. He gets the reference of the associated frame. Then, the optician sends the read frame reference as a request to the frame database which returns the corresponding geometrical frame information stored in the frame database. Actually, the optician reads the barcode with a dedicated equipment (barcode reader connected to the frame database) usually comprises means for reading the barcode (e.g. a scanner), means for transcripting the barcode into the frame reference corresponding to the selected trial spectacle, means for sending said reference to the centralized frame database and also means for receiving from said database the frame shape information in return. As detailed, this solution is much quicker than repetitive manual measurements realized by the optician on the frame each time a trial spectacle is selected by a wearer.

Alternatively, for saving a larger amount of the optician time, when the wearer performed his frame selection he can also, on his own, transmit the reference of the selected trial spectacle to the frame database by a manual operation. For example, the wearer operates the barcode reader or inputs the frame reference via a keyboard or a graphical user interface when the frame reference is also available for read on the tag.

Even these known methods for acquiring the geometrical shape of the frame are useful because they save the operating time of the optician; they still take time and require extra material in the frame selection place.

Alternative embodiments of the invention consist in acquiring more quickly the selected frame shape without any manual operation from optician or from the wearer at the frame selection place. These embodiments rely on a capture of at least one picture of the wearer wearing the selected trial spectacle and a posteriori extraction of the frame shape from the captured picture.

Advantageously said obtaining S3.1 step involves an extraction of said shape of frame from said at least one captured picture.

Alternative embodiments are performed by placing on the frame of each trial spectacle a tag comprising the frame reference and if possible the geometrical frame associated to the corresponding frame.

Advantageously, said extraction relies on a tag arranged on the spectacle frame worn by the wearer, wherein said tag appears at least partly in said at least one captured picture.

The frame shape extraction can be either direct or indirect. By "direct extraction", one means an evaluation of the frame shape directly from the captured picture, i.e. without any connection to the above mentioned frame database. This direct extraction is more advantageous because it makes unnecessary a connection between the picture processing side and the centralized frame database for getting the frame shape.

In a first exemplary embodiment of direct extraction, the tag is a barcode similar to the barcode described above and it is mandatorily placed on the spectacle frame so as to be apparent on the above-mentioned captured picture when the frame is worn by the wearer. The barcode comprises a data storage capacity enabling to store a large amount of data e.g. all information necessary for describing the 3D frame shape. And then the tag comprises the frame shape itself.

There is a tradeoff to perform on the size of the tag. On one hand, the larger is the tag size and the broader is its data storage capacity. On the other hand, the smaller is the tag size and the more convenient is the selection of the trial spectacle by the wearer. The barcode is read, at an image processing side, by performing a numerical analysis of the captured picture.

In a second advantageous exemplary embodiment, the tag is still a barcode placed so as to be apparent on a picture of the wearer captured in wearing time. But, the barcode is written with a particular ink either on the trial lens equipping the trial spectacle either directly on the frame. This particular ink is for example invisible when it is illuminated with a light in the visible spectrum and the ink is revealed, i.e. becomes apparent, in visible spectrum when illuminated under special condition (e.g. with Ultraviolet or Infra-Red light). In such a case, the picture capture is realized with a camera sensitive in the visible spectrum when the wearer is illuminated under specific lighting conditions making apparent the tag on the captured picture. This is advantageous because the tag is not visible for the wearer when he watches himself in the mirror wearing trial spectacles at the frame selection step. This releases the previously mentioned trade-off. The tag has a large size, and then a large data storage capacity. It does not represent a hindrance for the wearer when he selects the frame because it is invisible.

By "indirect extraction", one wishes to express that the extraction operates on the frame reference. It is the frame reference which is extracted from the captured picture. Then said frame reference is sent to a frame database already described for getting the frame shape corresponding to said extracted frame reference.

In a first and second exemplary embodiment of indirect extraction, the extraction is similar to the two previously described embodiments of direct extractions. But here, the tag comprises a data storage capacity enabling to store only a small amount of data. And then, the tag comprises the frame reference but not the frame shape itself.

The computing workload of image processing can either be centralized or distributed on various remote computers (cloud computing) for optimizing the computing costs or for optimizing the speed of the computing.

Advantageously the shape of the frame of the trial spectacle is input into the above mentioned frame databases by the frame manufacturers.

Advantageously the shape of frame of the trial spectacle is input into the above mentioned frame database in a collaborative way by the opticians themselves: when an optician receives a new trial spectacle having a new frame reference, he checks first if the frame reference is already stored in the frame database. If it is not the case, he performs all the measurements needed to retrieve the frame shape and he stores said information in the frame database under the new frame reference. Then, this new reference can be available for any optician connected over said frame database.

The frame selection place comprises said means for capturing at least one picture of said wearer wearing the selected spectacle frame, so as the tag placed on the spectacle frame appears on said at least one captured picture.

Advantageously a first preliminary check concerning the ability for the image processing to detect and read the tag in the captured picture is performed preferably shortly after the picture capturing time. Advantageously, this check is performed at the picture capturing side for enabling a quick warning to the wearer.

Advantageously a second preliminary check of the quality of the worn frame is additively performed in order to remove used trial spectacle (trial frame with dirty tag or unreadable tag).

The next step consists in measuring the precise position of the selected frame with respect to the face of the wearer in wearing time.

(S3) Measure of the Position of Spectacle Frame with Respect to the Wearer Face;

In the production of spectacles, it is necessary to cut the lenses designed to be fitted into the frame as a function of the choice of frame and of various parameters linked to the spectacle wearer. These parameters include in a non-limited way the distance between the pupils or in other words the horizontal distance between the eyes of the spectacle wearer, and various heights or distances with respect to the pupil of each eye.

Moreover, it is useful to know how the wearer wears its spectacle frame for personalizing the lens design.

The captured pictures are transmitted from the image capture side to the picture processing side where measurements of the position of selected spectacle frame with respect to the wearer face are performed.

According to an embodiment, said picture processing side 20 receives said three dimensional shape of said selected spectacle frame from a spectacle frame database 60. In an alternative embodiment, the wearer reads the barcode on his own with a barcode reader, or input the reference of the selected frame on a keyboard for sending it to a frame database.

Once the frame shape is determined by one of the above mentioned method, it provides a length reference. This enables to convert the distance between parts of objects shown in the captured picture (expressed in number of pixels) which can be evaluated by image processing into a distance in the object field. This avoids making appear a length reference on the captured picture for scaling the face of the wearer.

Figure 5:
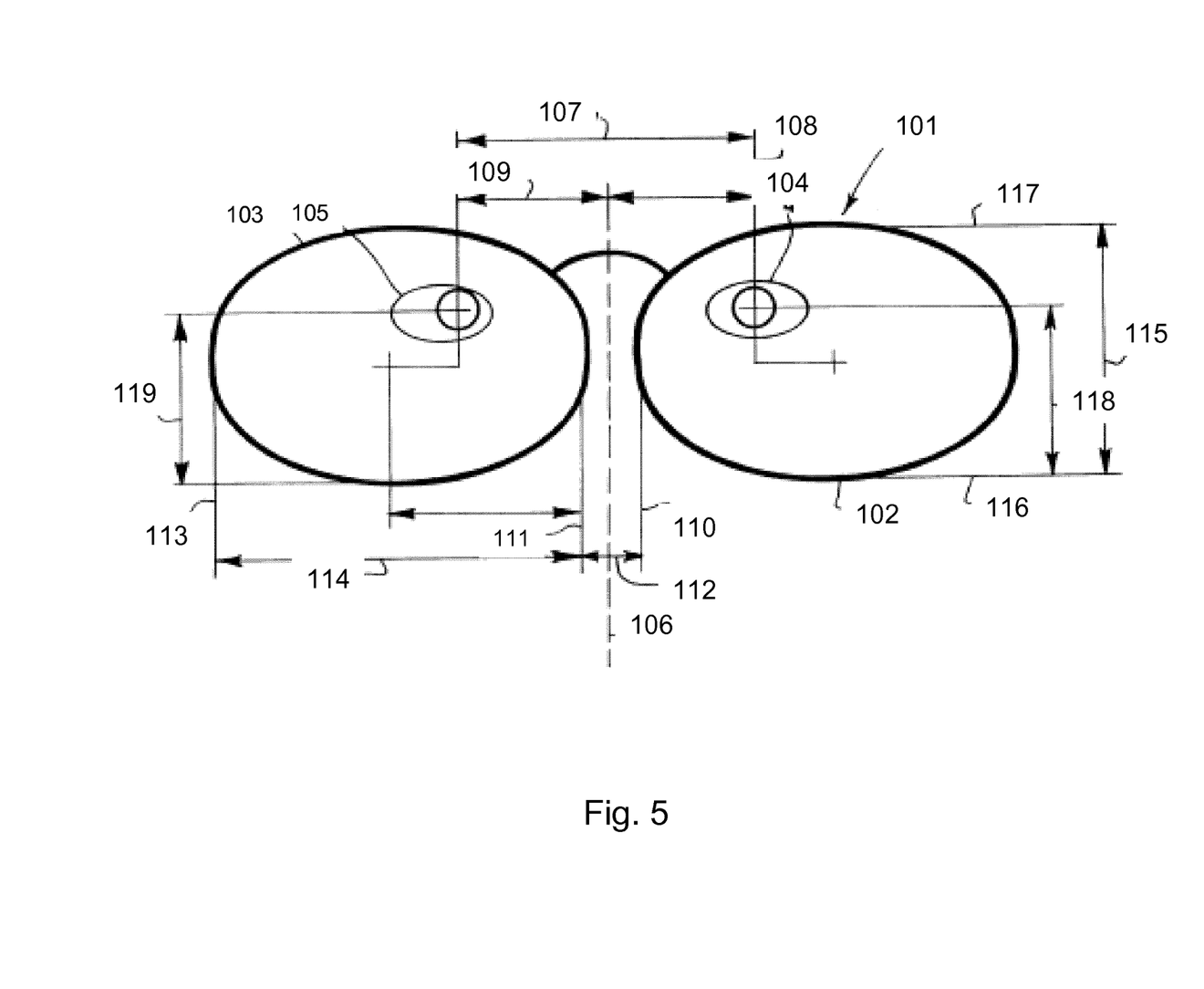
FIG. 5 shows diagrammatically the various measurement parameters for a spectacle wearer in a transverse plane.

FIG. 5 there can be seen a spectacle frame 101 comprising a left-hand half-frame 102 and a right-half frame 103, the spectacle wearer's left eye 104 and right eye 105 being shown diagrammatically. In order to prepare the spectacle glasses or lenses that suit the spectacle wearer and the chosen frame, it is necessary to know the position of the wearer's eyes with respect to the frame. The following parameters are currently used: The first is the distance between the centers of the two eyes of the wearer. On FIG. 3, the dashed line 106 represents the axis of the nose, the dimension 107 is the distance between the pupils and the dimensions 109 and 108 are the two right hand and left hand offsets. The distance between the two vertical straight lines (110, 111) tangential to the inside of each half-frame at the nose side is called the bridge. The dimension 112 in FIG. 3 corresponds to the bridge. The width of each half-frame, in other words the distance between the two vertical straight lines 111 and 113 tangential to the inside of each half-frame is called the 114 distance and the distance between the two horizontal straight lines 116 and 117 tangential to the inside of each half-frame is called the 115 distance. The intersection between the center line of the two horizontal tangential straight lines and the center line of the two vertical tangential straight lines is called the center of each half-frame. The distance between the center of the pupil of the left hand eye FIG. 104 (or, respectively, the right hand eye 105) and the horizontal straight line 116 tangential to the bottom of the inside of the left hand 102 (or, respectively, right hand 103) half-frame is called the left hand height 118 (or, respectively, right hand height 119). The horizontal or vertical distance between the center of each half-frame and the center of the pupil of the corresponding eye is called the horizontal or vertical, left hand or right hand, off-axis distance. The vertical distance between the center of the (right hand or left hand) pupil and the inside periphery of the frame below the center of the pupil is called the (right hand or left hand) depth of the frame below the pupil. The maximum distance between the center of the (right hand or left hand) pupil and the inner periphery of the corresponding frame portion is called the maximum (right hand or left hand) radius. The maximum radius enables one to determine what is the minimum diameter of lens that can be used.

The main task of the picture processing is to extract from the captured picture the fitting parameters needed for such as for example, the left hand height 118, the right hand height 119, the maximum (right hand or left hand) radius for each wearer eye. This picture processing side comprises computing means for performing extended image processing on captured picture at a plurality of picture capturing side.

Moreover, the frame selection place, also called below "picture capturing side", comprises means for capturing at least one picture showing at least partially the face of said wearer wearing the selected spectacle frame, so as a position of said spectacle frame with respect to the wearer face is extractable from said at least one captured picture. The captured pictures used for extracting said positions can be also used for acquiring the frame shape as discussed above.

Alternatively, captured pictures used for extracting said positions are different from captured pictures used for acquiring the frame shape.

Advantageously parameter measurements in transverse plane are performed thanks to the light spots provided by the comprised in the captured picture.

Advantageously, said means 20 for evaluating fitting parameters comprises said means 25 for extracting the three dimensional shape of said selected spectacle frame from said at least one captured picture.

The computing workload of said image processing can either be centralized or distributed on various remote computers (cloud computing) for optimizing the computing costs or for optimizing the speed of the computing.

Advantageously, said means 20 for evaluating fitting parameters further comprises means for inputting the three dimensional shape of said selected spectacle frame.

Advantageously, the means 20, 25 for evaluating fitting parameters is a dedicated server configured for receiving captured picture from a plurality of means 10 for capturing picture, wherein fitting parameters comprises at least said extracted frame positions and said obtained frame shape.

According to an embodiment, the method involves a further step of evaluating S2.1 whether said frame position with respect to the face of the wearer 1 is extractable from said at least one picture, wherein said further step S2.1 is carried out at said picture capturing side 10 or at said picture processing side 20 chronologically after said step S3.1 of obtaining frame shape and before said step S3 of processing.

The captured picture is quickly evaluated by calculation means for determining whether the frame position with respect to the face of the wearer is extractable from said at least one picture. If the number of spots in the captured image or their location, or even the picture quality is not evaluated as sufficient for determining the frame position with respect to the wearer face, the wearer is quickly informed and new pictures are to be captured at the image capturing side. Typical situation which cause trouble is when the wearer closes his eye, and the no spot can be seen on the cornea. At least another picture has to be captured. The advantage of this quick evaluation is to avoid that a picture transmitted to image processing side are declared useless or inoperable a posteriori. This is a first preliminary picture compliance check.

When the captured picture is evaluated as compliant for extracting fitting parameters, it is sent to an image processing side. The preliminary picture compliance check is performed very short time after the picture capturing time, at the picture capturing side or alternatively at the picture processing side which can be remote but linked at the picture capturing side through communicating means.

Advantageously, in parallel with the first preliminary check, or very short time after, a second preliminary check is performed. This second preliminary check concerns the consistency of the physiological data extracted form the picture of the wearer. Measurements are performed on the captured picture for determining parameters such as the distance between the wearer eyes, or the attitude of the wearer, and many other noticeable features. From these parameters, a detection is also performed of unusual situation such as, for example, a unusual wearer attitude (e.g. a wearer with a very bent back or a highly twisted neck) or a spectacle frame poorly placed on the wearer face during the frame capture time. This second preliminary check is further performed at the processing side. When one of these unusual situations is detected, the wearer is advised with chosen words to go preferably to a spectacle shop.

Advantageously, in parallel with the first and second preliminary check, or very shortly after, a third preliminary check is performed. This third check concerns the consistency of the collected data: mainly the wearer data (prescription), the selected lens options, and the selected frame shape. The goal of this third preliminary check is to give a quick feedback (Go/No go decision) to the wearer on the consistency of the data set he selected. The idea here is to give the information to the wearer that he can quit the picture capturing side with the assurance he will get a spectacle compliant with all his selections.

If an inconsistency is detected, for example between a high frame curving contour and a prescription with high value correction, the wearer is informed that he has to amend his selection of lens or of frame.

Advantageously, the three above mentioned preliminary checks are carried out at picture capturing side in the goal of providing a very quick return to the wearer.

Ordering Lens

Once the frame shape is obtained and the position of the frame is extracted, the collected data are gathered for forming fitting parameters.

In the first scenario where the optician still remains at the center of the ordering process, all collected data is concentrated at the optician shop. The fitting parameters are transmitted from the picture processing side to the lens ordering side via telecommunication means, e.g. secured communication on the internet.

At this point of the process, the optician only helped the wearer for selecting his frame. The frame shape, the frame position in regard with the wearer face is obtained automatically as described above, according various embodiments and mainly performed at the picture processing side. The optician already gets the wearer data and the selected lens options. From this, he selects a lens design adapted to the wishes of the wearer classically as in the prior art.

In the second scenario, where the optician is absent of the process, the fitting parameters are sent to a lens design side. The fitting parameters are transmitted from the picture processing side to the lens design side via telecommunication means, e.g. secured communication on the internet.

In addition the wearer data and the selected lens options are also transmitted to the lens design site 30. All the collected data constitutes a request to the lens design side.

Advantageously, said method involves further steps of:

Filtering S4 at the lens design side 30 at least one lens design from at least said wearer data, said fitting parameters and lens design rules;

Selecting S5 by an order side 50 a lens design among the at least one filtered lens design.

Said ordering S6 step consists in transmitting to said manufacturing side at least a lens order for said spectacle lens complying with said selected lens design.

Preferably, the lens design site is a lens design database comprising various lens design, rules for selecting lens design according to a request.

Of course, the filtering operations mentioned above depend on the lens options selected by the wearer and on the prescription. They also depend on the value of interpupillae distance and eye heights. But, extended filtering is available if the nature of frame positions information extracted from the captured picture allows to. In this case, the lens design can be personalized to the wearer needs at various levels. The filtering operation is advantageously performed by experts or by the execution of one or more stored sequences of instructions that are accessible to a processor.

A first advantage of this task organization is the speed of the process: there is no more bottleneck in the lens ordering process. There can be a plurality of these lens design sides over the world. Depending on the hour where the request is formed e.g. the hour at which wearer data, lens option, frame shape and frame position are known, the request id forwarded to more suitable lens design side for producing immediately at least one lens design.

A second advantage concerns the logistics. When a new lens design appears, it is easier and much quicker to make this evolution known at a small number of lens design side than at a very large number of optician shops.

Advantageously, the lens design includes price, estimated delivery time and other such information.

According to an embodiment, said selecting S5 step and ordering S6 step are initiated by said wearer: for example via wearer's home through internet.

From the reception of the lens order, the lens manufacturing side can proceed to the manufacturing of the lens: from the semi-finished lens to the edged lens through the application of selected coatings.

As the frame reference and frame shape is known through the fitting parameters, it is possible to order also the frame, to edge the lens in compliance with the frame, and to mount the manufactured lens onto the selected frame in order to provide very quickly a completely equipped spectacle.

Reference herein to "one embodiment" or "an embodiment" means that a particular feature, structure, or characteristic described in connection with the embodiment can be included in at least one implementation of the invention. The appearances of the phrase "in one embodiment" in various places in the specification are not necessarily all referring to the same embodiment, nor are separate or alternative embodiments necessarily mutually exclusive of other embodiments.

The invention claimed is:

1. A method for ordering a spectacle lens for a wearer, said method comprising:
    capturing, by a camera, at least one picture showing at least a portion of a face of said wearer wearing a selected spectacle frame, the at least one captured picture being sufficient so that a position of said selected spectacle frame on the wearer's face is extractable from said at least one captured picture;
    determining, by processing circuitry, a frame shape of the selected spectacle frame by:
        reading from within the at least one captured picture, a barcode tag having data storage capacity appearing within the at least one captured picture, the barcode tag being encoded with at least information describing a three dimensional shape of the selected spectacle frame;
    responsive to the reading, directly extracting at least the information describing the three dimensional shape from the barcode tag without connecting to a database;
    processing, by the processing circuitry, said at least one captured picture and obtaining, by the processing circuitry, the position of said selected spectacle frame on the wearer's face using the three dimensional shape of the selected spectacle frame extracted from the at least one captured picture; and
    selecting, by a server, said spectacle lens complying with said selected spectacle frame and said three dimensional shape of said selected spectacle frame, said position of said selected spectacle frame on the wearer's face, and wearer data, wherein said wearer data comprises at least a prescription for the wearer.

2. The method according to claim 1, further comprising evaluating whether said position of said selected spectacle frame on the wearer's face is extractable from said at least one captured picture.

3. A system for supplying a spectacle lens for a wearer, said system comprising:
    a camera configured to capture at least one picture showing at least a portion of a face of said wearer wearing a selected spectacle frame, the at least one captured picture being sufficient so that a position of said selected spectacle frame on the wearer's face is extractable from said at least one captured picture;
    processing circuitry configured to
        determine a frame shape of the selected spectacle frame by:
            reading, from within the at least one captured picture, a barcode tag having data storage capacity appearing within the at least one captured picture, the barcode tag being encoded with at least information describing a three dimensional shape of the selected spectacle frame, and
            responsive to the reading, directly extracting at least the information describing the three dimensional shape from the barcode tag without connecting to a database, and
        process said at least one captured picture and obtain the position of said selected spectacle frame on the wearer's face using the three dimensional shape of the selected spectacle frame extracted from the at least one captured picture; and,
    a server configured to select said spectacle lens complying with said selected spectacle frame and said three dimensional shape of said selected spectacle frame, said position of said selected spectacle frame on the wearer's face, and wearer data.

4. The system according to claim 3, wherein the server is configured to receive captured pictures from a plurality of cameras.

5. The system according to claim 3, wherein said camera is configured to control lighting conditions of the wearer's face when said camera operates.

6. The system according to claim 3, further comprising a processor configured to indicate whether said position of said selected spectacle frame on the face of the wearer is extractable from said at least one captured picture.

* * * * *